United States Patent
Minogue et al.

(10) Patent No.: US 9,545,514 B2
(45) Date of Patent: Jan. 17, 2017

(54) SMART GARMENT TECHNOLOGY

(75) Inventors: Conor Minogue, Kinvara (IE); Michel Las-Saulzais, Athenry (IE); Joseph M. Rochford, Ballyhaunis (IE)

(73) Assignee: BMR Research & Development Limited (IE)

( * ) Notice: Subject to any disclaimer, the term of this patent is extended or adjusted under 35 U.S.C. 154(b) by 700 days.

(21) Appl. No.: 12/302,694

(22) PCT Filed: May 30, 2007

(86) PCT No.: PCT/EP2007/055242
§ 371 (c)(1),
(2), (4) Date: Jan. 5, 2009

(87) PCT Pub. No.: WO2007/138071
PCT Pub. Date: Dec. 6, 2007

(65) Prior Publication Data
US 2009/0105795 A1    Apr. 23, 2009

(30) Foreign Application Priority Data

Jun. 1, 2006 (GB) .................................. 0610824.5

(51) Int. Cl.
  *A61N 1/32* (2006.01)
  *A61N 1/36* (2006.01)
  *A61B 5/00* (2006.01)
  A61B 5/0402 (2006.01)
  A61B 5/0488 (2006.01)
  A61N 1/04 (2006.01)

(52) U.S. Cl.
CPC ......... *A61N 1/36003* (2013.01); *A61B 5/6804* (2013.01); *A61B 5/6814* (2013.01); *A61N 1/0484* (2013.01); *A61N 1/321* (2013.01); *A61N 1/36014* (2013.01); *A61B 5/0402* (2013.01); *A61B 5/0488* (2013.01); *A61B 2560/0412* (2013.01); *A61N 1/0452* (2013.01); *A61N 1/0472* (2013.01)

(58) Field of Classification Search
CPC .......................... A61N 1/36014; A61B 5/6804
USPC ................. 600/388–390, 393; 607/115, 149
See application file for complete search history.

(56) References Cited

U.S. PATENT DOCUMENTS

| | | | | |
|---|---|---|---|---|
| 5,078,134 A | * | 1/1992 | Heilman et al. | 607/4 |
| 5,487,759 A | | 1/1996 | Bastyr | 607/114 |
| 5,562,707 A | * | 10/1996 | Prochazka et al. | 607/2 |
| 5,620,483 A | | 4/1997 | Minogue | 607/115 |

(Continued)

FOREIGN PATENT DOCUMENTS

| | | |
|---|---|---|
| JP | 8-508897 A | 9/1996 |
| JP | 9-327521 A | 12/1997 |
| JP | 2005-237941 A | 9/2005 |

*Primary Examiner* — Carl H Layno
*Assistant Examiner* — Jennifer Ghand
(74) *Attorney, Agent, or Firm* — DLA Piper LLP (US)

(57) ABSTRACT

A method and apparatus for making a connection with a part of a body to transfer an electromagnetic signal for a predetermined purpose, the apparatus including: a garment including one or more electrode capable of passing the signal to or from the part of the body; and a controller for controlling the nature of or processing the signal dependant on one or more parameters in order to vary the nature of the signal dependant on the purpose; wherein at least one parameter of the one or more parameters is stored on a data storage device included in the garment.

25 Claims, 6 Drawing Sheets

(56) References Cited

U.S. PATENT DOCUMENTS

| | | | |
|---|---|---|---|
| 7,072,721 B1* | 7/2006 | Trent | 607/149 |
| 2002/0077688 A1* | 6/2002 | Kirkland | 607/142 |
| 2004/0122483 A1 | 6/2004 | Nathan et al. | 607/49 |
| 2004/0127937 A1* | 7/2004 | Newton | 606/202 |
| 2004/0254624 A1 | 12/2004 | Johnson | 607/149 |
| 2005/0131288 A1* | 6/2005 | Turner et al. | 600/391 |
| 2007/0089800 A1* | 4/2007 | Sharma | 139/388 |
| 2007/0293917 A1* | 12/2007 | Thompson et al. | 607/72 |
| 2008/0021355 A1* | 1/2008 | Huster et al. | 601/149 |

* cited by examiner

SMART GARMENT TECHNOLOGY

CROSS-REFERENCE TO RELATED APPLICATIONS

This application is a §371 of International Application No. PCT/EP2007/055242, with an international filing date of May 30, 2007 (WO 2007/138071 A1, published Dec. 6, 2007), which claims priority of British Patent Application No. 0610824.5, filed Jun. 1, 2006, the subject matter of which is incorporated by reference.

BACKGROUND

It is a common requirement to have to make electrical connections to the body surface for measurement of electrical activity originating within the body or to deliver electrical energy into the body. Usually it is necessary to position one or more electrodes in contact with the skin at anatomical locations specific to the intended application. It is also common to devise attachment means such as garments, wraps or braces which incorporate one or more electrodes on their skin facing surface, which locate on the body at target anatomical locations when the garment is worn by the user. Usually such garments incorporate wiring, which connect the electrodes to an electronic module by means of a detachable connector. U.S. Pat. No. 6,885,896 describes such a system where an electronic module interfaces to a holster which is fixed on an internally wired abdominal belt and delivers electrical stimulation signals to the electrodes mounted on the skin facing surface of the belt.

Similar systems can be envisaged for treatment of the knee, back, shoulder etc. and indeed the literature has many examples of garments and braces for different parts of the body incorporating electrodes.

Given a selection of such garments or other attachment means intended for a range of body parts, it is desirable that they would interface to a common electronic module. This would be less costly than having a dedicated electronic module for each garment type. In a typical clinic, it is possible to envisage a selection of single-patient use garments for a range of anatomical sites and a stock of identical electronic controllers which can attach to any garment. The problem with using a common controller for all garments is that the controller would have to be configured by the user or therapist for each garment type prior to use. Furthermore, since a given garment becomes assigned to a particular patient, and the controllers can be swapped or replaced between patients, it is necessary that the controller become personalised to that patient. For this reason it is desirable that the controller can be configured for the type of garment it is connected to and that the treatment for the specific patient can be selected.

The number and size of electrodes on each garment type may be different and the electrical signals applied to each electrode will inevitably be specific to the garment type and the intended treatment. The controller could be manually programmable through data input by the therapist to take account of different garment designs and treatment parameters however this process is error prone.

Traditionally electrotherapy has used electrical generators which have one or more channels, each channel of which has a dedicated pair of electrodes. When the pair of electrodes for a given channel are placed on the body an electrical circuit is completed which allows the therapeutic current to flow in the body between the electrodes of a pair. The path of the current in the body is largely defined by the position of the electrodes on the body. When multiple channels are applied to the body then they are generally isolated so that no current flows between channels. The current pathways on the body are limited to the areas between the individual elements of each pair. Recently the advantage of treating a group of electrodes on the body as an uncommitted array has been recognised. This allows the controller to select which electrode or combination of electrodes is used to source current at any given time and which combination of the remaining electrodes of the array is used as a sink. This allows the controller to set up current pathways between any electrodes of the array, not just between the hardwired pairs of the traditional method. Moreover, it is advantageous to change the electrode groupings during the course of the treatment to, for example, avoid fatiguing the same muscles. The electrode array selection, and the way that selection might be changed with time, is likely to be anatomy specific. Since garments incorporating arrays of electrodes may be designed for different body parts, it is inevitable that electrode selections to produce anatomically appropriate current pathways will require the selection of different electrode array elements. For example a shoulder brace and a knee brace may both have arrays of 4 electrodes; however different electrode combinations will apply and these combinations are likely to change in different ways for each during treatment. The controller could be designed to accept data input from the therapist to handle this configuration, however this is not a user-friendly solution.

Electrodes in garments may have different surface areas and therefore the current density will vary for a given applied current. It is important therefore that a stimulator be able to calculate and thereby keep below a defined current density limit in order to keep within safety limits. It is therefore necessary to somehow enter data to the controller describing the electrode surface areas. Furthermore, electrodes in electrotherapy garments may have different electrical impedance properties depending on geometry, anatomical location, construction and electrolyte type. It can be important for the controller to be able to validate the quality of the connection prior to delivering energy into the body.

Arrays of electrodes are used to acquire signals from the body surface in electrophysiological monitoring. Depending on the anatomical location of the electrodes and the signals they are intended to monitor, there can be very significant differences in signal processing parameters. For example an Electro-cardiographs (ECG) signal recovered from the chest has very different signal amplitude and spectral characteristics compared to an Electro-myograph (EMG) signal recorded from the arm.

Even within the various lead configurations of an ECG there are wide ranges of acceptable signal parameters. A multi-purpose controller capable of interfacing with a range of such garments would have to have input data which allows it to process signals detected on its input terminals. This data could be input by the user however this would be tedious and error prone.

Garments may easily be configured with other signal monitoring sensors, such as temperature, pressure, force, acceleration, displacement. Insofar as these signals need to be processed by the controller, input data is required which identifies the signal type, the amplifier gain and filter pass bands required to acquire them, as well as normal limits for the signal. Such setup data could be entered by the user, however again this is not a user friendly solution.

There is a need therefore for electronic modules to automatically configure themselves depending on what garment type they are connected to. There have been some attempts to solve related problems in the past. Bastyr, U.S. Pat. No. 5,487,759 described a brace which incorporated electrodes for treating the knee. It featured a keyed connector which, in effect, implemented a 3 bit binary code to enable a controller to select which one of a selection of carrier frequencies to use. Different carrier frequencies were required for the different electrode sizes that would occur in different garments. Bastyr does not recognise any type of automatic garment recognition to enable definition of the performance of the controller.

Further and significant problems with the Bastyr solution, include the fact that solution is limited to only 3 encoding bits. Also the controller is pre-programmed to deliver one out of 8 possible carrier frequencies which were encoded to the device when it was manufactured and this creates another problem. If an additional garment were to be introduced to the range at some later time, which needed a carrier frequency not included as one of the pre-defined set, then it would be necessary to produce a new controller with updated carrier frequencies. This is because the 3 bit code merely identifies the brace and does not provide the actual treatment parameters which the controller has to use with that brace. The code was not re-writable so the configuration could not be changed.

Furthermore Bastyr has described a stimulation system which includes two channels of stimulation each of which is hardwired to a dedicated pair of lead wires and electrodes. This uses biphasic stimulation in which current flows in one direction between electrodes of a pair for a period and then flows in the opposite direction between the same pair for a period. There is no requirement to re-configure the electrical connection of the electrodes depending on the target garment, or the selected treatment for a target garment. Nor is there any consideration of the requirement to specify and store information on electrode area, electrode impedance or wear out profiles.

A partial solution to this problem is to allow the user select the target garment from a menu provided on the controller. Again this is error prone and also inflexible in that it requires that all the necessary data has been previously loaded into the controller.

It could therefore be helpful to provide a system which overcomes at least some of the problems of the prior art.

It could also be helpful to provide a system which allows a suitably programmed electronic controller to interface to a range of body worn wired garments and to recognise which garment type is connected, to select the appropriate connections to direct electrical signals to the appropriate combination of electrodes for the intended treatment with that garment, and to select the treatment timing and other parameters so that it can synthesize the necessary signals on the appropriate terminals.

It could still further be helpful to provide a system which allows a suitably programmed electronic controller to interface to a range of body worn wired garments and to recognise which garment type is connected, to select the appropriate connections for detection of specific biological signals and to apply signal processing steps appropriate to the signal type and intended use.

SUMMARY

According to one aspect, there is provided an apparatus for making a connection with a part of a body to transfer an electromagnetic signal for a predetermined purpose, the apparatus including: a garment including one or more electrodes capable of passing the signal to or from the part of the body; and a controller for controlling or for measuring the signal dependant on one or more parameters; wherein at least one parameter of the one or more parameters is stored on a data storage device included in the garment.

According to a second aspect, there is provided a method of transferring an electromagnetic signal to or from a part of a body for a predetermined purpose, the method including: wearing a garment including one or more electrodes capable of passing the signal to or from the part of the body; and controlling or measuring the signal dependant on one or more parameters in accordance with the predetermined purpose; the method further comprising storing at least one parameter of the one or more parameters on a data storage device included in the garment.

One of the key features is that the data required by the controller to recognize and cooperate with a wired garment is stored in a data storage device built into garment. It is also envisaged that the controller stores data on patient treatment history in the data memory located on the garment. In this way a common controller can interface with a range of garment types and automatically upload data from the garment, which enables it to deliver appropriate signals to the electrodes and/or correctly process signals detected on nominated electrodes.

A further advantage of this system is that a range of garments can be developed over a number of years and each of them can be compatible with a previously designed electronic controller. This is because the garments contain the treatment specification data and the controller simply loads this data to its on board microcomputer at start up and uses this data to produce the necessary stimulation signals at the appropriate terminals and/or or to appropriately process signals detected at nominated electrodes. This feature also allows treatment data to be changed as new therapies are developed since it is simply a matter of rewriting data in the garment memory.

The attachment means can take other forms, such as a brace, headset, limb clamp or self adhering electrodes. In the latter example the electrode adheres to the skin directly and conductive connection to the controller is done by means of a leadwire. The data storage device envisaged in this invention can be integrated into such an electrode assembly. This can be done by integration of the memory chip directly into the electrode assembly. Separate electrical connection to the chip terminals could be provided by additional leadwires.

Many of the problems previously identified are solved by this approach. The patient or therapist does not have to identify which garment is connected, or to enter treatment specification data or select from a range of treatment options. They do not have to be concerned with how the electrodes are connected in the garment or to make selections which direct the electrical stimulus to the right sets of electrodes. They do not have to make selections about which electrodes contain relevant biological signals and what signal processing means are required to interpret them.

A further advantage of this approach is that treatment data logging can use the garment memory for storage. For example, information identifying the patient, the treatment history with the system, records of physiological measurements taken, condition of electrodes, service and replacement data. This information can be used to alert the user when it is time to clean or replace the electrodes.

A garment containing a data storage device can store information to enable a connected controller to interpret signals appearing on its terminals. Furthermore, the aspects of the patient history relevant to the signals being measured can be stored on the garment, for example alarm limits for heart rate variation.

BRIEF DESCRIPTION OF THE DRAWINGS

Reference will now be made by way of example, to the accompanying drawing, in which.

DETAILED DESCRIPTION

Figure 1:
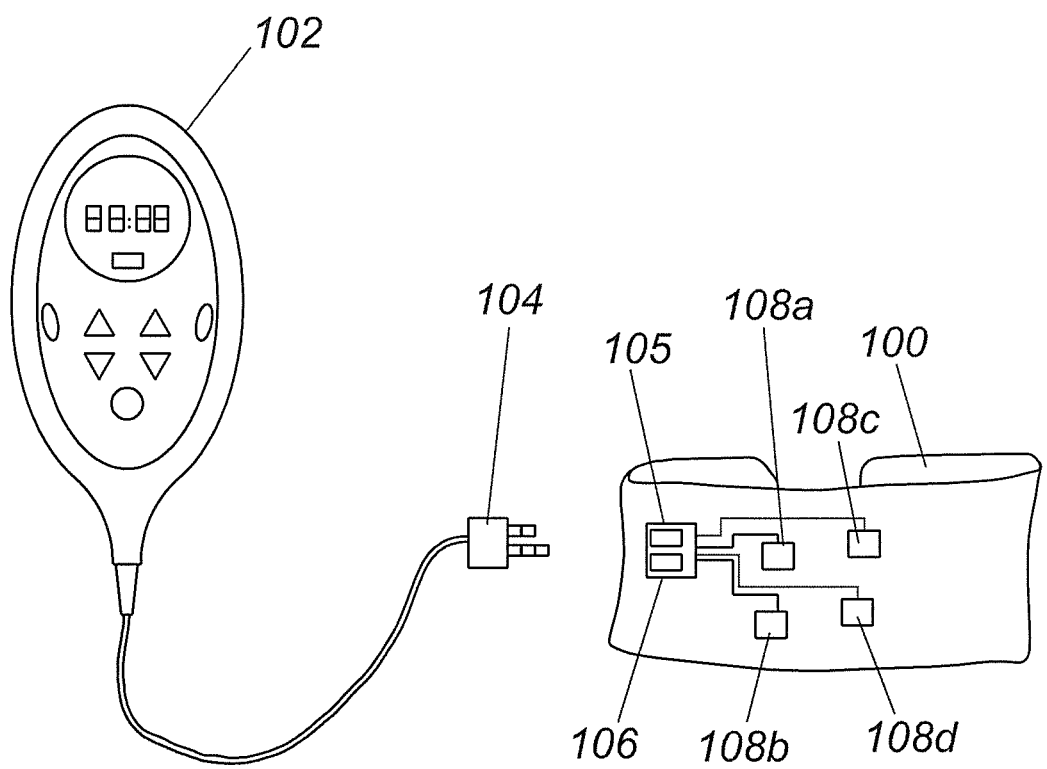
FIG. 1 is a diagram of a garment including wires and a controller.

FIG. 1 shows a typical wired garment 100 and controller 102 which connect together in an appropriate manner for example a plug or other connector 104. The controller may be an electronic module and the wired garment also contains a component 105 supporting a data storage device 106. For example the data storage device may be a serial data electrically erasable programmable read only memory (EEPROM) or any other appropriate type of storage device.

The clothing in FIG. 1 is in the form of a body belt with four separate electrodes 108a, 108b, 108c, 108d, which each impart the required stimulation at a particular point of the body wearing it. The belt may be equipped with fastening means for holding the belt in place and may also include some external indicators to enable the belt to be correctly positioned on the body.

Figure 2:
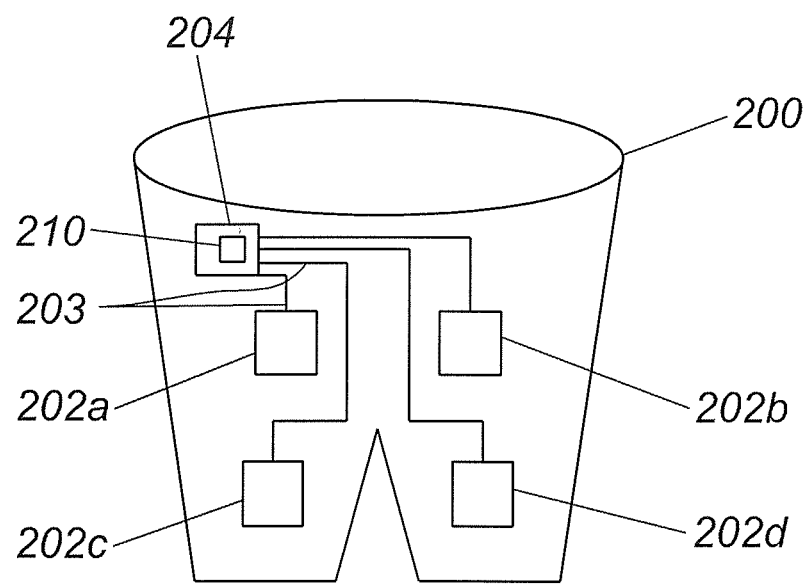
FIG. 2 is a diagram of a further garment including wires and connectors.
Figure 3:
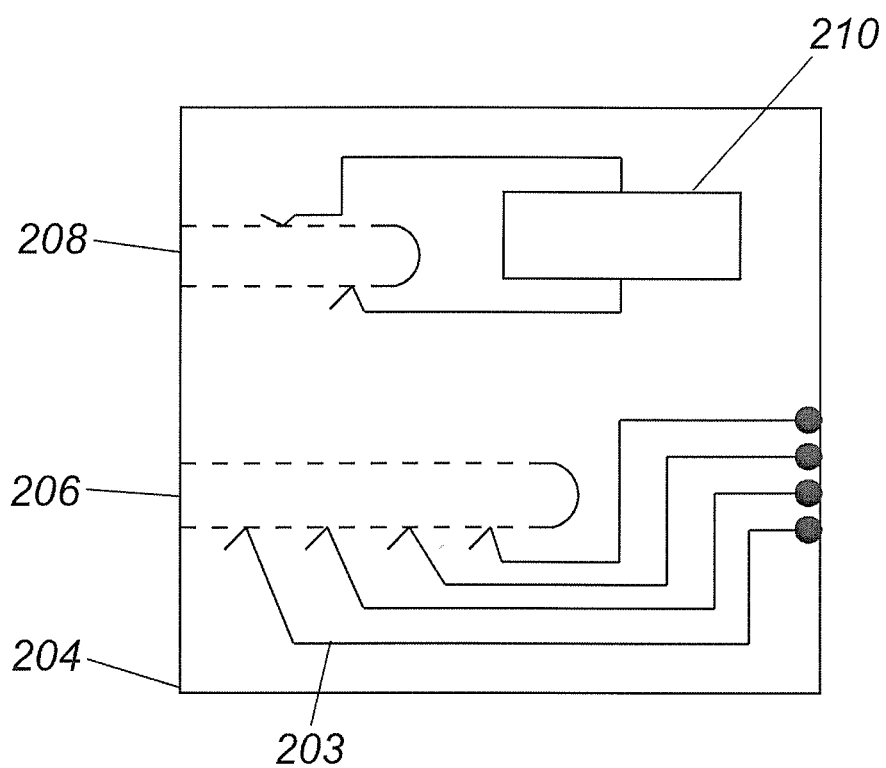
FIG. 3 is a diagram of one type of device which may be incorporated into a garment.

Referring to FIG. 2 a different garment 200 is shown. This garment includes four electrodes 202a-d each connected to a component 204. The component is shown in more detail in FIG. 3 and is similar in both FIGS. 1 and 2. The component 204 includes two female connections 206 and 208 for receiving the prongs of plug 104 (as shown in FIG. 1). The electrodes 202a-d are connected to one of the female connections 206 via connection wires 203. The data storage device 210 (equivalent to 106 in FIG. 1) is connected to the other connection 208. The data storage device may be a "one wire" serial EEPROM memory device such as that supplied by Dallas Semiconductor and is integrated into the Data Storage Element on the garment. Upon connection to the controller using the plug 104 and switch on, the controller can read the contents of the serial EEPROM and thereby configure the controller for delivery of the required treatment for a particular person and that garment.

Entry of configuration data to the memory on the garment can be accomplished in various ways. It can be entered at manufacture through use of a special jig which interfaces with connector 208. Data can also be entered after manufacture, by a suitably programmed computer and an adapter which converts data format for communication to the memory via connector 208. The controller 102 may also be programmed to have a configuration mode, whereby data and options selected by a user can be transferred and stored in the garment memory.

Figure 4:
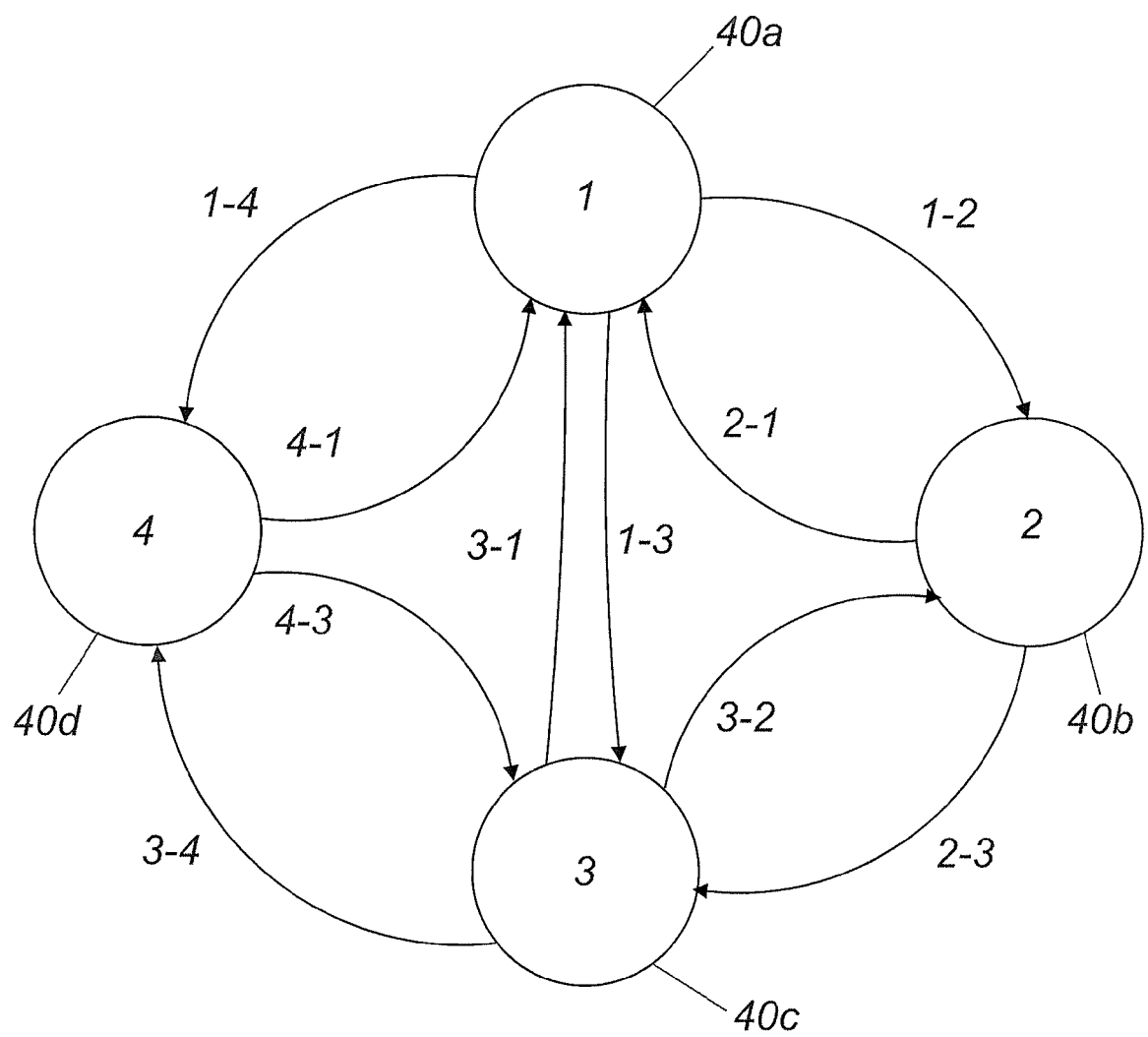
FIG. 4 is a diagram showing electrodes and pathways.

FIG. 4 shows how the electrodes 40a-d and pathways (lines with arrows in the figure) used in delivery of the pulse may be defined in a four electrode example. Such information could be provided on a pulse by pulse basis, but more likely it would be provided for groups of pulses or entire pulse trains. These options could be coded in the data storage means.

It will be appreciated that for more or less electrodes different combinations and numbers of interconnections and paths can be envisaged. In addition, by use of certain types of pulsing and electrode combinations any type of pulse or electric pattern can be generated as will be described in greater detail below.

The electronic module contains a microcomputer and drive circuitry which generates electrical pulses on the set of one or more output terminals, which terminals are, in use, intended to be connected to electrodes on the garment in contact with the body. The controller can deliver electrical drive signals to the terminals such as to cause currents to flow between selected terminals and thereby between the electrodes which are connected to the terminals. The microcontroller program uses stored data as input to calculate the precise timing of the signals to be the applied to the output terminals.

Figure 7:
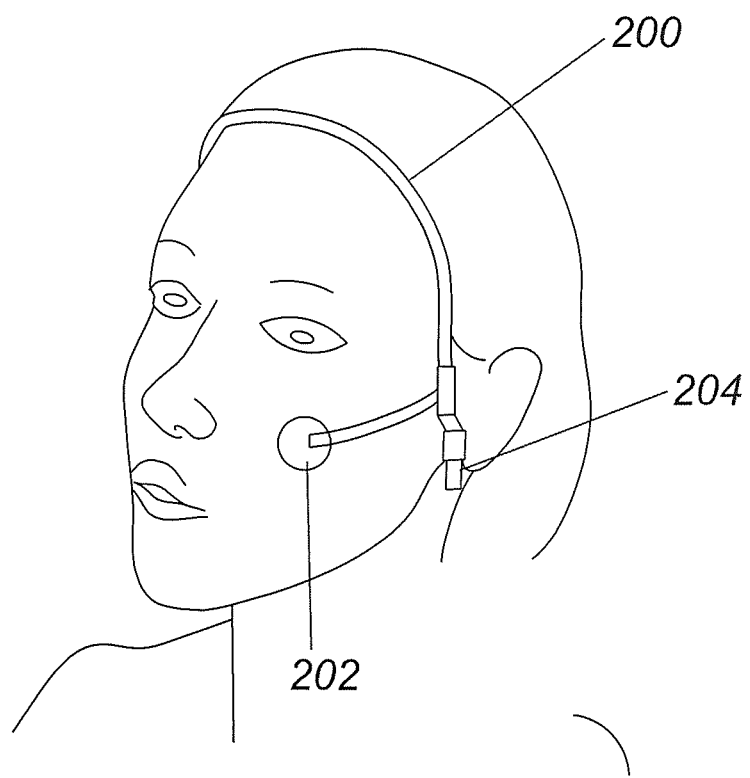
FIG. 7 illustrates an alternative attachment means which is directed at stimulation of the facial muscles.

FIG. 7 shows an attachment means for supporting electrodes on the face in accordance with the present invention. The data storage element 210 (not shown in FIG. 7) is integrated into the connector module 204 located on the headset attachment means.

The term "garment" is intended to include anything which is worn on or in contact with a body. The attachment means of FIG. 7 are thus encompassed within the definition of the term garment, as is any other form of attachment means howsoever attached to the body. The attachment means can be braces, frames, wires, adhesives or any other form. The only requirement is that there are one or more electrodes and a storage element for data supported on or in contact with the body.

The setup and configuration of the stimulation controller to co-operate with a body electrode accessory such as a wired garment requires the input of data sufficient to specify the particular requirements of interfacing with that garment for the intended treatment. Various types of data are required and include:

Data specifying the stimulation pulse train waveform;
Data specifying the electrical connections to electrodes;
Data specifying the trigger options for the stimulation;
Data specifying signal acquisition parameters; and
Data specifying particulars of the patient and the selected therapy.

Figure 5:
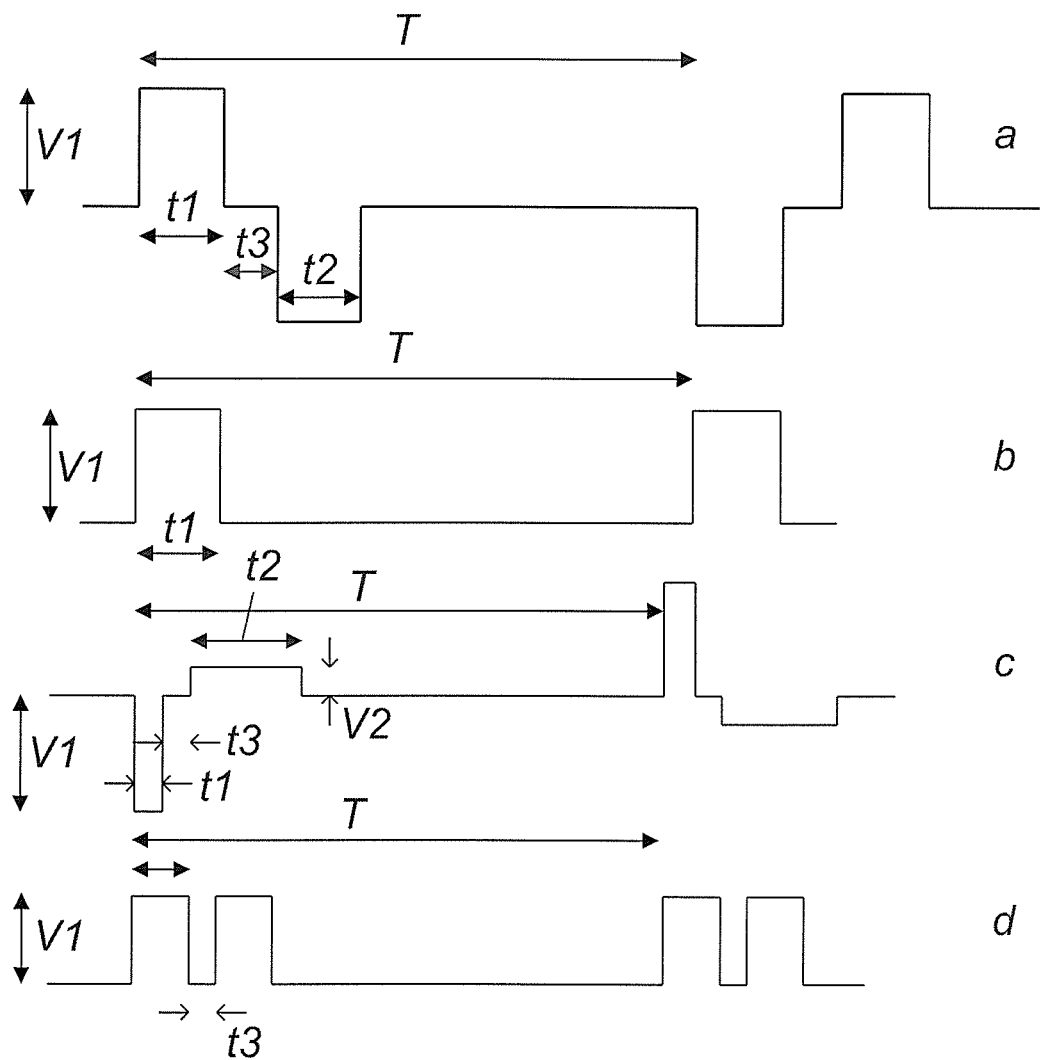
FIG. 5 is a timing diagram for waveforms used in electrical stimulation.

FIG. 5 shows some typical waveform that could be used in the electrical stimulation which will be described in greater detail below and include:

Symmetric biphasic pulse, with alternating leading phase polarity;
Monophasic pulses;
Pulse doublets; and
Asymmetric biphasic pulse with alternating leading phase polarity. Such pulse geometries can be described by identifying the waveform type from a list similar to that shown above and specifying certain parameters, such as Leading Phase Polarity P, Leading Phase Amplitude $V_1$, Leading Phase Duration $t_1$, Trailing Phase duration $t_2$, Interphase interval $t_3$, Trailing Phase amplitude $V_2$. The Pulse Repetition Rate may be defined in terms of the Inter-Pulse Interval (T). These pulse parameters can be different for each channel of stimulation and therefore can be expressed as an array, for example $t_1(1)$, $t_2(2)$, . . . $t_2(i)$ etc.

Figure 6:
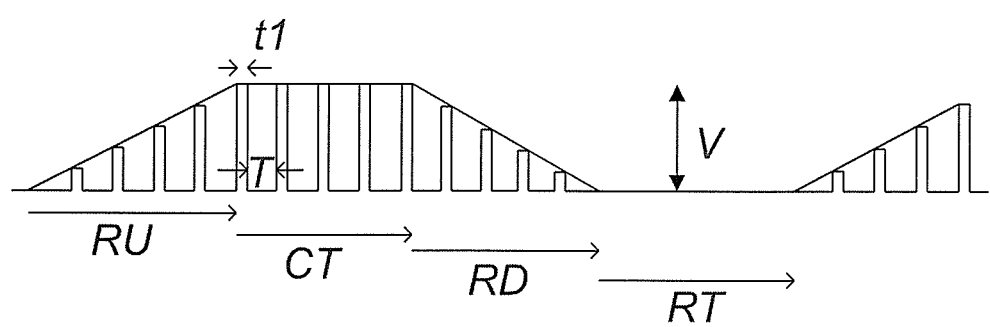
FIG. 6 is a pulse train for a channel.

FIG. 6 shows the main elements of an amplitude modulated pulse train which can be described by the Maximum Signal Amplitude V, Ramp_Up Time RU, Contraction-Time CT, Ramp_Down Time RD, Off-time RT, Modulation type, Depth of Modulation M. There may be several such trains on different channels and the time relationship between them also needs to be defined as Phase Delay. Alternative modulation schemes can also be specified, for example, frequency modulation, pulse width modulation, phase modulation. The treatment may be broken into segments, each with a defined duration in seconds. The stimulation parameters for each segment can be different and in this way complex treatment sequences involving changes in frequency, pulse width, waveform type etc can be encoded.

Table A summarizes data required to specify the pulse train of a treatment segment, and typical ranges for the values which arise. For data storage efficiency, an indirect index can be stored as a value, and the actual value thereby recovered from a lookup table in the controller. For example, a typical pulse train used in electrical stimulation applied could be characterized by the following data set.

TABLE A

Pulse Train Timing Description.

| Parameter | Typical Range |
|---|---|
| Number of user channels | 1 to 4 |
| Pulse Frequency(n)* | .1 to 200 Hz |
| Leading Phase duration(n) | 50uS to 10000 us |
| Trailing Phase Duration(n) | 50uS to 10000 us |
| ON time (Contraction) (n) | 0.5 to 99 seconds |
| OFF time (Relaxation) | 0.5 to 99 seconds |
| Ramp Up time | 0.0 to 9.9 seconds |
| Ramp Down Time | 0.0 to 9.9 seconds |
| Treatment segment time | 1 to 99 minutes, or indefinite |
| Maximum Amplitude(n) | 10 to 100 mA |
| Pulse Type(n) | Biphasic/Monophasic/Doublet |
| Modulation | Amplitude/Frequency/Pulse Width |
| Inter-Channel Delay(n) | 0.0 to 9.9 seconds |
| Channel tracking | Alternate/Synchronous |
| Depth of Modulation | 0 to 100% |
| Pulse Frequency in Relaxation | 1 to 40 Hz |
| Phase Duration in Relaxation | 50 to 400uS |
| Flip alternate leading phase polarity | Yes or No |
| Segment duration | 1 to 10,000 seconds, or indefinite |

*The argument indicates channel specific values. For example; Pulse Frequency(i) denotes the pulse frequency on channel i.

The microcontroller may also select which output terminals to apply the drive signals to. For example at any given time it may select a certain subset of the set of terminals to be anodes, another subset of the set of terminals to be cathodes. The controller applies signals to a constant current drive circuit which causes a stimulation current to flow between the anode set and the cathode set. These assignments can be changed with time to create bidirectional current flow, and to create current flows between different terminals. Data specifying the electrode selection to be used to produce a succession of pulses can be stored in various forms.

The simplest form is a bit map memory 2N bits wide, where N is the number of electrodes in use. The high N bits are used to identify which electrodes are to be used as anodes, while the low N bits are used to identify which electrodes are to be used as cathodes. Electrodes unselected as either are left floating electrically. A 2N bit record like this can be used for each phase of a sequential stimulation, with an additional record which specifies the phase duration. A multiphase stimulation sequence can be specified to any required level of detail, limited only by the data storage capacity and speed of retrieval in real time.

Clearly there are many data structures in which such information can be represented, and there are many data compression possibilities. An important aspect of the present information is that some or all of this data is stored on the data storage device located in the electrode attachment accessory or garment.

The possible electrical connections are illustrated by way of example in Table B.

TABLE B

Electrical Connection

| | |
|---|---|
| Number of Electrodes | 1 to N |
| Allowed pathways. | Example |
| | 1-2, 2-1, 1-3, 3-1 |
| | Note for N = 24, all possible paths are 1-2, 2-1, 1-3, |
| | 3-1, 1-4, 4-1, 2-3, 3-2, 2-4, |
| | 4-2, 3-4, 4-3 |
| Electrode area | Area of each electrode in cm$^2$ 1 thru N |
| Pathway impedance | Calibrated pathway impedance limits (Ohms) |

Frequently in electrical stimulation therapy systems there are further options which may be selected. For example the stimulation may be selected to be triggered rather than free running, and the trigger conditions themselves may be programmable. The trigger source could be a hand switch or foot switch. A typical table of such trigger options by many of example could be as shown in Table C.

TABLE C

Trigger Options

| Mode | Burst/Continuous |
|---|---|
| Trigger Mode | None/gated/+ve edge monostable/−ve edge monostable/dual gated. |
| Analog input threshold | None/level/+ve level/−ve level |
| Trigger count | 1 to N events. |
| Trigger source | Handswitch/external port terminal. |

When the garment has a signal monitoring function then the data storage device may be used to provide information to the controller on how to process the signal. The electrodes to be used are identified and further information on acceptable electrode impedance, amplifier gain and filter settings are also provided as is shown by many of example in Table D.

TABLE D

Monitoring Characteristics

| Characteristic | Example for ECG monitoring. |
|---|---|
| Differential electrodes | 1-2 |
| Reference electrode | 3 |
| Electrode impedance | 1k |
| Gain required | 800 |

TABLE D-continued

Monitoring Characteristics

| Characteristic | Example for ECG monitoring. |
|---|---|
| High pass filter corner frequency | 8 |
| Low pass filter corner frequency | 40 |

There may also be a requirement to store patient specific data, for example patient identification number or patient name, start date, program number selected, treatment session duration in minutes, total treatment hours to be completed, total treatment hours actually completed, intensity limit on each channel, intensity level reached on each channel, average intensity level used on each channel, date of next appointment. In addition the device may log patient measurements such as body temperature during session, heart rate, blood pressure, maximum force produced, muscle fatigue index etc.

A data file specifying at least some of the above information is stored in a memory device located within the garment. When the controller is connected to the garment and switched on the controller loads the file into its on-board memory and uses this information to deliver the electrical stimulation to the output terminals, and/or to process signals recovered on the electrodes identified. During and after the treatment the controller may store various treatment specific data back in the memory device located in the garment, for example, the average intensity used, total time used, number of treatments completed etc.

While the description here has referred to a wired connection between the controller and the garment, clearly it is possible to have the garment identification and data exchange between the garment and the controller implemented in a wireless link.

An important characteristic is that the data storage device containing the data describing the medical treatment is stored to some extent at least in the garment.

While our apparatus has been particularly shown and described with reference to a preferred example, it will be understood that various changes in form and detail may be made therein without departing from the spirit, and scope of this disclosure.

The invention claimed is:

1. Apparatus for making a connection with a part of a body to transfer an electromagnetic signal for a predetermined purpose comprising:
a garment comprising one or more electrodes that pass the signal to or from the part of the body;
a controller that is electronically detachable from the garment and controls the nature of, or measures, the signal dependent on one or more parameters, the controller comprising output terminals capable of connecting to the one or more electrodes; and
a second electrically programmable data storage device included in the garment wherein at least one parameter of the one or more parameters is stored;
wherein the controller determines a selection of output terminals capable of connecting to the one or more electrodes said signal being delivered to said selection of output terminals to cause a current to flow between selected electrodes from the one or more electrodes, and wherein the controller comprises a first data storage device, and the controller automatically loads the one or more parameters from the second electrically programmable data storage device to the first data storage device to configure the controller to deliver the signal to the selected output terminals.

2. The apparatus of claim 1, wherein the second data storage device includes parameters relating to a user of the garment and the predetermined purpose.

3. The apparatus of claim 1, wherein the second data storage device includes parameters relating to selection of electrodes.

4. The apparatus of claim 1, wherein the electrodes are connected to the controller by a connector.

5. The apparatus of claim 4, wherein the second data storage device forms part of the connector.

6. The apparatus of claim 1, wherein the controller changes characteristics of the signal dependent on the parameters.

7. The apparatus of claim 6, wherein the changes to the signal characteristics are associated with the predetermined purpose.

8. The apparatus of claim 1, wherein the controller changes the selected electrodes dependent on the parameters.

9. The apparatus of claim 1, wherein the second data storage device includes a memory to record parameters derived from the body.

10. The apparatus of claim 1, wherein the one or more electrodes are oriented in the garment in a predetermined pattern.

11. The apparatus of claim 10, wherein the signal passes from one electrode to another dependent on the predetermined purpose.

12. The apparatus of claim 1, wherein the signal includes a pulse train comprising two or more component signal elements.

13. The apparatus of claim 1, wherein the garment is an item of clothing.

14. The apparatus of claim 1, wherein the garment is a brace.

15. The apparatus of claim 1, wherein the garment is an adhesively attached electrode.

16. A method of transferring an electromagnetic signal to or from a part of a body for a predetermined purpose comprising:
wearing a garment including one or more electrodes that pass the signal to or from the part of the body;
controlling or measuring the signal dependent on one or more parameters in accordance with the predetermined purpose with a controller being electronically detachable from the garment and comprising output terminals that are capable of connecting to the one or more electrodes, said controller comprising a first data storage device;
storing at least one parameter of the one or more parameters on a second electronically programmable data storage device included in the garment; and
selecting output terminals to which the signal is delivered to cause a current to flow between selected electrodes from the one or more electrodes, wherein the output terminals are capable of connecting to the one or more electrodes;
wherein the selecting step comprises automatically loading the one or more parameters from the second data storage device to the first data storage device to configure the controller to deliver the signal to the selected output terminals.

17. The method of claim 16, further comprising including parameters relating to the user of the garment and the predetermined purpose in the second data storage device.

18. The method of claim 16, further comprising connecting the or each electrode to the controller.

19. The method of claim 18, further comprising forming the second data storage device as part of the connection.

20. The method of claim 19, further comprising changing the signal characteristics in association with the predetermined purpose.

21. The method of claim 16, further comprising changing the characteristics of the signal dependent on the parameters.

22. The method of claim 16, further including recording parameters derived from the body as a result of a signal incident thereon on a memory.

23. The method of claim 16, further comprising orienting the one or more electrodes in the garment in a predetermined pattern to deliver a selected type of signal.

24. The method of claim 22, further comprising passing the signal from one electrode to another dependent on the predetermined purpose.

25. The method of claim 16, comprising producing a pulse train comprising two or more component signal elements.

* * * * *